United States Patent [19]

Winter et al.

[11] Patent Number: 5,679,812

[45] Date of Patent: Oct. 21, 1997

[54] COMPOUND USEFUL FOR THE PREPARATION OF A 1-OLEFIN POLYMER

[75] Inventors: Andreas Winter, Kelkheim; Volker Dolle, Kelkheim; Jürgen Rohrmann, Neufahrn; Walter Spaleck, Liederbach, all of Germany

[73] Assignee: Hoechst Aktiengesellschaft, Frankfurt, Germany

[21] Appl. No.: 480,648

[22] Filed: Jun. 7, 1995

Related U.S. Application Data

[62] Division of Ser. No. 750,760, Aug. 22, 1991, which is a continuation of Ser. No. 571,040, Aug. 21, 1990, abandoned, which is a continuation of Ser. No. 508,481, Apr. 11, 1990, abandoned, which is a continuation of Ser. No. 321,366, Mar. 9, 1989, abandoned.

[30] Foreign Application Priority Data

Mar. 12, 1988 [DE] Germany .......................... 38 08 268.3

[51] Int. Cl.⁶ ........................................................... C07F 7/10
[52] U.S. Cl. .................................. 556/7; 556/11; 556/12; 556/13; 556/19; 556/20; 556/21; 556/42; 556/43; 556/52; 556/53; 502/155; 526/127; 526/160; 526/943
[58] Field of Search ............................. 556/7, 11, 12, 556/13, 19, 20, 21, 27, 42, 43, 52, 53

[56] References Cited

U.S. PATENT DOCUMENTS

| | | | |
|---|---|---|---|
| 4,522,982 | 6/1985 | Ewen | 525/240 |
| 4,536,484 | 8/1985 | Lacombe et al. | |
| 4,542,199 | 9/1985 | Kaminsky et al. | |
| 4,701,432 | 10/1987 | Welborn, Jr. | |
| 4,769,510 | 9/1988 | Kaminsky et al. | |
| 4,794,096 | 12/1988 | Ewen | 502/107 |
| 4,808,561 | 2/1989 | Welborn, Jr. | |
| 4,897,455 | 1/1990 | Welborn, Jr. | 526/129 |
| 4,933,403 | 6/1990 | Kaminsky et al. | |
| 4,937,299 | 6/1990 | Ewen et al. | |
| 5,017,714 | 5/1991 | Welborn, Jr. | |
| 5,084,534 | 1/1992 | Welborn, Jr. et al. | |
| 5,103,030 | 4/1992 | Rohrmann et al. | |
| 5,120,867 | 6/1992 | Welborn, Jr. | 556/12 |
| 5,314,973 | 5/1994 | Welborn, Jr. | |

FOREIGN PATENT DOCUMENTS

| | | |
|---|---|---|
| 029 108 | 12/1984 | Australia . |
| 058 914 | 12/1986 | Australia . |
| 067 773 | 6/1987 | Australia . |
| 079 165 | 3/1988 | Australia . |
| 020 435 | 2/1989 | Australia . |
| 627588 | 9/1961 | Canada . |
| 1 317 411 | 5/1993 | Canada . |
| 0 127 530 | 12/1984 | European Pat. Off. . |
| 0 128 046 | 12/1984 | European Pat. Off. . |
| 0 129 368 | 12/1984 | European Pat. Off. . |
| 0 185 918 | 7/1986 | European Pat. Off. . |
| 0 197 319 | 10/1986 | European Pat. Off. . |
| 0 206 794 | 12/1986 | European Pat. Off. . |
| 0 226 463 | 6/1987 | European Pat. Off. . |
| 0 232 595 | 8/1987 | European Pat. Off. . |
| 0 260 999 | 3/1988 | European Pat. Off. . |
| 0 284 707 | 10/1988 | European Pat. Off. . |
| 0 284 708 | 10/1988 | European Pat. Off. . |
| 0 302 424 | 2/1989 | European Pat. Off. . |
| 0 320 762 | 6/1989 | European Pat. Off. . |
| 2 539 133 | 7/1989 | France . |
| 37 26 067 | 2/1989 | Germany . |

OTHER PUBLICATIONS

Ewen et al., "Crystal Structures and Stereospecific Propylene Polymerization with Chiral Hafnium Metallocene Catalysts", J. Am. Chem. Soc. 109, pp. 16544–6545 (1987).

Kaminsky et al., "Transition Metals and Organometallics as Catalysts for Olefin Polymerization", Proceedings of an International Symposium, Hamburg, Sep. 21, 1987–Sep. 24, 1987, pp. 281–289 (1988).

Kaminsky et al., "Olefinpolymerization with Highly Active Soluble Zirconium Compounds Using Aluminoxane as Cocatalyst", Makromol. Chem., Macromol. Symp. 3, pp. 377–387 (1986).

Grant & Hackh's Chemical Dictionary (3d Ed.) p. 192 (1969).

Moore, *Physical Chemistry*, Prentice–Hall, NJ (1955) p. 116.

*Primary Examiner*—David W. Wu
*Attorney, Agent, or Firm*—Connolly & Hutz

[57] ABSTRACT

A very efficient catalyst system for the polymerization of 1-olefins consists of an aluminoxane and a metallocene which is a compound of the formula I

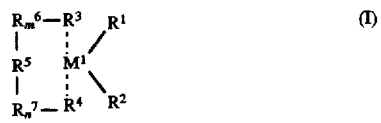

in which R$^1$ and R$^2$ denote hydrogen atoms, halogen atoms or hydrocarbon radicals and R$^3$ and R$^4$ are mononuclear or polynuclear hydrocarbon radicals which can form a sandwich structure with the central atom and which are linked to one another by a —R$^6_m$—R$^5$—R$^7_n$— bridge containing a hetero atom and consisting of one or several members.

The catalyst system produces polymers having a high molecular weight and excellent grain morphology.

7 Claims, No Drawings

COMPOUND USEFUL FOR THE PREPARATION OF A 1-OLEFIN POLYMER

This application is a divisional of application Ser. No. 07/750,760 filed Aug. 22, 1991 which is a continuation of Ser. No. 07/571,040 filed Aug. 21, 1990 now abandoned which, in turn, is a continuation of Ser. No. 07/508,481 filed Apr. 11, 1990, now abandoned which again, in turn, is a continuation of Ser. No. 07/321,366 filed Mar. 9, 1989, now abandoned.

The invention relates to a process for the preparation of 1-olefin polymers having high isotacticity, narrow molecular weight distribution, high molecular weight and excellent grain morphology.

Soluble metallocene compounds based on bis (cyclopentadienyl)zirconium-alkyl or bis(cyclopentadienyl) zirconium halide in combination with oligomeric aluminoxanes are known from the literature. These systems can be used to polymerize ethylene and propylene with moderate activity, however, no isotactic polypropylene is obtained.

Furthermore, the catalyst system bis(cyclopentadienyl) diphenyltitanium/methylaluminoxane is known to be capable of converting propylene into stereoblock polymers, that is, polypropylene having more or less long isotactic sequences (cf. U.S. Pat. No. 4,522,982). Distinct disadvantages of this catalyst system are the polymerization temperatures (0° C. to −60° C.) which are irrelevant for industrial-scale operations and the entirely unsatisfactory catalyst activities.

The preparation of isotactic polypropylene can be achieved by means of ethylenebis(4,5,6,7-tetrahydro-1-indenyl)zirconium dichloride together with an aluminoxane in a suspension polymerization reaction (cf. EP-A 185, 918). The polymer has a narrow molecular weight distribution, which is advantageous for certain applications, for example for high-performance injection molding. At the same time, the catalyst system has a series of shortcomings.

The polymerization is carried out in toluene, which has to be purified at great expense and freed from moisture and oxygen. Moreover, the bulk density of the polymer is too small and the grain morphology and particle size distribution unsatisfactory. However, a particular disadvantage of this known process is that at the polymerization temperatures which are of interest in industry only polymers having an unacceptably low molecular weight can be prepared.

A special preactivation method of the metallocene/aluminoxane system, which leads to a remarkable increase in the activity of the catalyst system and to a significant improvement in the grain morphology of the polymer has also been proposed (cf. DE 3,726,067). It is true that the preactivation increases the molecular weight, but no significant increase can be achieved.

Furthermore, catalysts based on ethylenebis(indenyl) hafnium dichloride and ethylenebis(4,5,6,7-tetrahydro-1-indenyl)hafnium dichloride and methylaluminoxane, by means of which higher-molecular-weight polypropylenes can be prepared by suspension polymerization, are known (cf. J. A. Ewen et al., J. Am. Chem. Soc. 109 (1987) 6544). However, under industrially relevant polymerization conditions, the grain morphology of the polymers thus produced is unsatisfactory and the activity of the catalysts used is comparatively low.

The object was to find a catalyst which produces polymers having improved grain morphology and high molecular weight in high yields.

It has been found that the object can be achieved by using certain hetero-atom bridged metallocene systems.

Accordingly, the invention relates to a process for the preparation of a 1-olefin polymer by polymerization of a 1-olefin of the formula R—CH=CH₂ in which R is an alkyl group having 1 to 28 carbon atoms, or copolymerization of these olefins with one another or with ethylene, at a temperature from −60° to 200° C., at a pressure from 0.5 to 60 bar, in solution, in suspension or in the gas phase, in the presence of a catalyst which consists of a metallocene as transition metal compound and an aluminoxane of the formula (II)

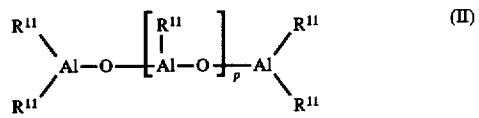

for the linear type and/or of the formula (III)

for the cyclic type, where in the formulae (II) and (III) $R^{11}$ denotes a $C_1$–$C_6$-alkyl group and p is an integer from 2 to 50, which comprises carrying out the polymerization in the presence of a catalyst whose transition metal component is a compound of the formula (I)

in which $M^1$ is a metal from the group consisting of titanium, zirconium, vanadium, niobium and tantalum, $R^1$ and $R^2$ are identical or different and denote a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, $R_3$ and $R_4$ are identical or different and denote a mononuclear nuclear or polynuclear hydrocarbon radical which can form a sandwich structure with the central atom, $R^5$ denotes

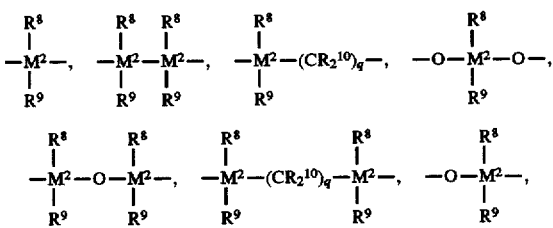

=BR⁸, =AlR⁸, —Ge—, —Sn—, —O—, —S—, =S=O, =SO₂, =NR⁸, =PR⁸ or =P(O)R⁸, in which $R^8$, $R^9$ and $R^{10}$ are identical or different and denote a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^8$ and $R^9$ or $R^8$ and $R^{10}$ each form a ring together with the atoms linking them, $M^2$ denotes silicon, germanium or tin and q denotes 1, 2 or 3, $R^6$ and $R^7$ are identical or different and denote a $=CR^8R^9$ group, in which $R^8$ and $R^9$ have the abovementioned meaning, m and n are identical or different and denote zero, 1 or 2, where m+n is zero, 1 or 2, and whose activator is also an aluminoxane of the formula (II) or (III).

Various transition metal compounds can be used for the process according to the invention. They are stereorigid chiral metallocenes of the formula (I)

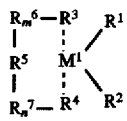  (I)

$M^1$ is a metal from the group consisting of titanium, zirconium, vanadium, niobium and tantalum, preferably titanium or zirconium, in particular zirconium.

$R^1$ and $R^2$ are identical or different and denote a hydrogen atom, a $C_1$–$C_{10}$-alkyl group, preferably a $C_1$–$C_3$-alkyl group, a $C_6$–$C_{10}$-aryl group, preferably a $C_6$–$C_8$-aryl group, a $C_2$–$C_{10}$ $C_1$-alkenyl group, preferably a $C_2$–$C_4$-alkenyl group, a $C_7$–$C_{40}$-arylalkyl group, preferably a $C_7$–$C_{10}$-arylalkyl group, a $C_7$–$C_{40}$-alkylaryl group, preferably a $C_7$–$C_{12}$-alkylaryl group, a $C_8$–$C_{40}$-arylalkenyl group, preferably a $C_8$–$C_{12}$-alkenyl group or a halogen atom, preferably chlorine.

$R^3$ and $R^4$ are identical or different, preferably identical, and denote a mononuclear or polynuclear hydrocarbon radical which together with the central atom can form a sandwich structure. Examples of this type of radical are the indenyl, tetrahydroindenyl or cyclopentadienyl group and heteroaromatic ligands.

$R^5$ is

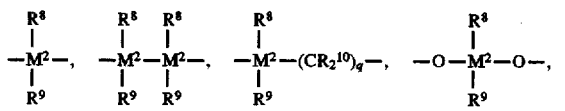

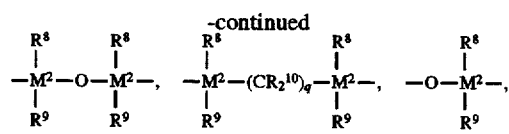

$=BR^8$, $=AlR^8$, $—Ge—$, $—Sn—$, $—O—$, $—S—$, $=S=O$, $=SO_2$, $=NR^8$, $=PR^8$ or $=P(O)R^8$, in which $R^8$, $R^9$ and $R^{10}$ are identical or different and denote a hydrogen atom, a halogen atom, preferably fluorine, a $C_1$–$C_{10}$-alkyl group, preferably $C_1$–$C_4$-alkyl group, a $C_6$–$C_{10}$-aryl group, preferably a $C_6$–$C_8$-aryl group, a $C_2$–$C_{10}$-alkenyl group, preferably a $C_2$–$C_4$-alkenyl group, a $C_7$–$C_{40}$-arylalkyl group, preferably a $C_7$–$C_{10}$-aryl-alkyl group, a $C_8$–$C_{40}$-arylalkenyl group, preferably a $C_8$–$C_{12}$-arylalkenyl group or a $C_7$–$C_{40}$-alkylaryl group, preferably ably a $C_7$–$C_{12}$-alkylaryl group, or $R^8$ and $R^9$ or $R^8$ and $R^{10}$ each form a ring together with the atoms linking them.

$M^2$ is Si, Ge or Sn and q is 1, 2 or 3, $R^5$ is preferably $=SiR^8R^9$, $—S—$, $=S=O$ or $=PR^8$, $R^6$ and $R^7$ are identical or different and denote a $=CR^8R^9$ group, in which $R^8$ and $R^9$ have the abovementioned meaning, m and n are identical or different and denote zero, 1 or 2, where m+n is zero, 1 or 2. Preferably, m and n are zero or 1.

The optically active metallocenes are used as racemate for the preparation of highly isotactic poly-1-olefins. However, it is also possible to use the pure R or S forms. An optically active polymer can be prepared by means of these pure stereoisomeric forms. However, it is necessary to separate off the meso form of the metallocenes, since the polymerization-active center (the metal atom) in these compounds is not longer chiral due to reflection symmetry on the central metal and can therefore not produce any highly isotactic polymers.

The principle of the separation of the stereoisomers is known.

The metallocenes described above can be prepared according to the following reaction scheme:

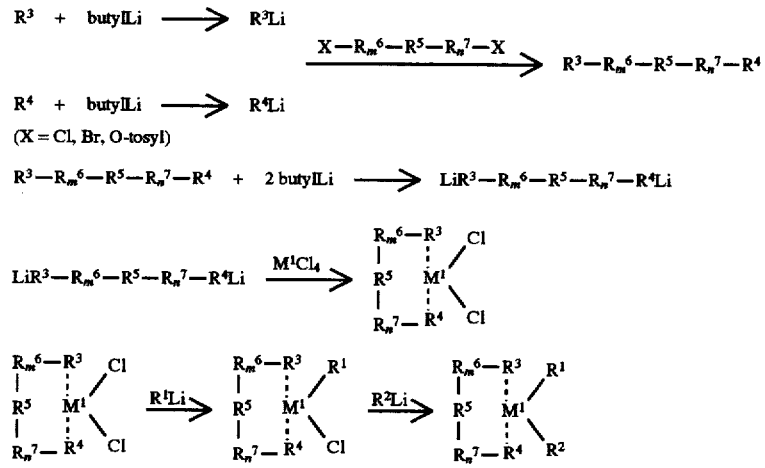

The metallocene compounds which are particularly preferably used are rac-bisindenyl(arylalkylsilyl)zirconium dichloride and rac-bisindenyl(dialkylsilyl)zirconium dichloride.

The activator is an aluminoxane of the formula (II)

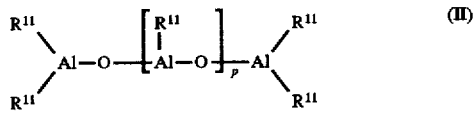

for the linear type and/or of the formula (III)

for the cyclic type. In these formulae, $R^{11}$ denotes a $C_1$–$C_6$-alkyl group, preferably methyl, ethyl or isobutyl, in particular methyl, and p denotes an integer from 2 to 50, preferably 15 to 40.

The aluminoxane can be prepared, for example, by different methods.

In one of the processes, finely powdered copper sulfate pentahydrate is suspended in toluene, and trialkylaluminum aluminum is added in a glass flask under inert gas at about −20° C. in such an amount that about 1 mole of $CuSO_4 \times 5H_2O$ is present for every four aluminum atoms. After slow hydrolysis with the elimination of alkane, the reaction mixture is left at room temperature for 24 to 48 hours, in the course of which it may have to be cooled to prevent the temperature from rising above 30° C. The aluminoxane dissolved in toluene is then freed from copper sulfate by filtration, and the solution is concentrated under a vacuum. It is assumed that in this preparation process the low-molecular-weight aluminoxanes are condensed to higher oligomers with the elimination of trialkylaluminum.

Aluminoxanes are also obtained by reacting trialkylaluminum, preferably trimethylaluminum, dissolved in an inert aliphatic or aromatic solvent, preferably heptane or toluene, at a temperature from −20° to 100° C. with hydrated aluminum salts, preferably aluminum sulfate. In this reaction, the ratio by volume between the solvent and the alkylaluminum used is 1:1 to 50:1—preferably 5:1—and the reaction time, which can be controlled by the elimination of the alkane, is 1 to 200 hours—preferably 10 to 40 hours.

Of the hydrated aluminum salts, in particular those are used which are highly hydrated. Particular preference is given to hydrated aluminum sulfate, in particular the compounds $Al_2(SO_4)_3 \times 18H_2O$ and $Al_2(SO_4)_3 \times 16H_2O$ which are particularly highly hydrated at 18 mole and 16 mole of $H_2O$/mole of $Al_2(SO_4)_3$.

A further variation for the preparation of aluminoxanes consist in dissolving trialkylaluminum, preferably trimethylaluminum, in the suspending agent which was initially introduced into the polymerization kettle, preferably in the liquid monomer, in heptane or toluene, and then reacting the aluminum compound with water.

Apart from the processes for the preparation of aluminoxanes described above, there are others which are useful.

It is preferred to preactivate the metallocene with an aluminoxane of the formula (II) and/or (III) before it is used in the polymerization reaction. This significantly increases the polymerization activity.

The preactivation of the transition metal compound is carried out in solution. Preferably, the metallocene is dissolved in a solution of the aluminoxane in an inert hydrocarbon. Suitable inert hydrocarbons are aliphatic or aromatic hydrocarbons.

Preferably, toluene is used.

The concentration of the aluminoxane in the solution is in the range from about 1% by weight to the saturation limit, preferably 5 to 30% by weight, in each case relative to the entire solution. The metallocene can be used in the same concentration, but preferably it is used in an amount of $10^{-4}$–1 mole per mole of aluminoxane. The preactivation time is 5 minutes to 60 hours, preferably 5 to 60 minutes. The activation is carried out at a temperature from −78° C. to 100° C. preferably 0° to 70° C.

A considerably longer preactivation is possible, usually has no activity-increasing or activity-reducing effect, but can be quite appropriate for the purpose of storage.

Preactivation hardly increases the molecular weight of the polymer at all. Preferably, the same aluminoxane is used for the preactivation and the polymerization.

The catalyst to be used according to the invention is employed for the polymerization of 1-olefins of the formula R—CH=CH$_2$, in which R denotes an alkyl radical having 1 to 28 carbon atoms, preferably 1 to 10 carbon atoms, in particular one carbon atom, for example propylene, 1-butene, 1-hexene, 4-methyl-1-pentene and 1-octene. Propylene is particularly preferred. Furthermore, the catalyst is also used for the copolymerization of these olefins with one another or with ethylene, it being possible to incorporate in the product more than 50% by weight of ethylene by polymerization.

The polymerization is carried out in a known manner in solution, in suspension or in the gas phase, continuously or batchwise, in one or more steps at a temperature from −60° to 200° C., preferably −20 to 120, in particular 0° to 80° C. The pressure is 0.5 to 60 bar. Polymerization in the pressure range from 5 to 60 bar, which is of particular interest in industry, is preferred.

The metallocene compound is employed in a concentration, relative to the transition metal, of $10^{-3}$ and $10^{-7}$, preferably $10^{-4}$ to $10^{-6}$ mole of transition metal per $dm^3$ of reactor volume. The aluminoxane is employed in a concentration of $10^{-4}$ to $10^{-1}$ mole, preferably $10^{-3}$ to $10^{-2}$ mole, per $dm^3$ of solvent or per $dm^3$ of reactor volume. Higher concentrations are, however, in principle also possible.

It is advantageous first to stir the aluminoxane for a few minutes together with the polymerization liquid phase before the addition of the metallocene. The stirring time is preferably 10 to 30 minutes. However, it is also possible to stir for a shorter period of time without any great losses and a longer stirring time has no significant effect on the result of polymerization.

The polymerization is carried out in an inert solvent customary for the Ziegler low-pressure process. For example in an aliphatic or cycloaliphatic hydrocarbon; such a solvent is, for example, butane, pentane, hexane, heptane, isooctane, cyclohexane, methylcyclohexane. A benzine or hydrogenated diesel oil fraction which has been carefully freed from oxygen, sulfur compounds and moisture can also be used. Toluene is also suitable. Preferably, the monomer to be polymerized is used as solvent or suspending agent. The molecular weight of the polymers can be regulated in a known manner; preferably, hydrogen is used for this. The duration of the polymerization can be of any desired length, since the catalyst system to be used according to the invention shows only a slight time-dependent decrease of the polymerization activity.

By means of the process according to the invention, it is possible to prepare polymer powders consisting of compact spherical particles having a very narrow particle size distribution and a high bulk density. The polymer powder is distinguished by very good free-flowing properties.

The polymer has a high molecular weight, a very narrow molecular weight distribution and a high isotacticity.

The use of hetero atom-bridged metallocenes produces polymers of a higher molecular weight than does the use of metallocenes which only have a hydrocarbon bridge.

The examples which follow are intended to illustrate the invention. The symbols have the following meanings:

VN=viscosity number in cm³/g, $M_w$=average molecular weight in g/mol, $M_w/M_n$=molecular weight distribution determined by gel permeation chromatography (GPC) and II=isotactic index determined by $^{13}$C-NMR spectroscopy

EXAMPLE 1

A dry 16 dm³ kettle was flushed with nitrogen and charged with 10 dm³ of liquid propylene. 50 cm³ of a methylaluminoxane solution in toluene (corresponding to 68 mmol of Al, average oligomerization degree n=23) were then added, and the batch was stirred at 30° C. for 15 minutes. At the same time, 14.3 mg (0.028mmol) of rac-bisindenyl(phenylmethylsilyl)zirconium dichloride were dissolved in 25 cm³ of a methylaluminoxane solution in toluene (34 mmol of Al) and preactivated by being left to stand for 15 minutes. The solution was then added to the kettle. The polymerization system was brought to a temperature of 70° C. and maintained at this temperature for 2 hours. 2.21 kg of polypropylene were obtained. The activity of the metallocene was therefore 77.4 kg of PP/g of metallocene×h.

VN=50.2 cm³/g, $M_w$=42,600, $M_w/M_n$=2.3, II=94%, SD=449 g/l, fines content of the powder <100 µm: 0.6%. The polymer product was obtained in the form of large spherical particles having a narrow particle size distribution. Particle size distribution in the polymer:

| Sieve tray [µm] | Proportion [%] | Sum [%] |
|---|---|---|
| <100 | 0.6 | 0.6 |
| 100–200 | 1.2 | 1.8 |
| 200–300 | 0.8 | 2.6 |
| 300–400 | 1.9 | 4.5 |
| 400–500 | 2.5 | 7.0 |
| 500–630 | 4.4 | 11.4 |
| 630–800 | 5.7 | 17.1 |
| 800–1000 | 43.3 | 60.4 |
| 1000–1250 | 19.6 | 80.0 |
| 1250–2000 | 15.2 | 95.2 |
| 2000–2500 | 3.9 | 99.1 |
| >2500 | 0.9 | 100.0 |

$d_{50} = 1000 \, \mu m, \, S = \ln \frac{d_{50}}{d_{15}} = 0.33.$

EXAMPLE 2 AND COMPARATIVE EXAMPLE A

In an experiment analogous to Example 1 and using rac-bisindenyl(dimethylsilyl)zirconium dichloride as catalyst, a polymer having a VN of 45.8 cm³/g, an $M_w$ of 36,375 and an $M_w/M_n$ of 2.4 was obtained. Repeating the same procedure with racethylenebisindenylzirconium dichloride only gave the following values:

VN=32.5 cm³/g, $M_w$=20,700, $M_w/M_n$=2.1.

EXAMPLE 3

The procedure of Example 1 was repeated, except that 30.9 mg (0.06 mmol) of rac-bisindenyl(phenylmethylsilyl) zirconium dichloride were used, the polymerization time was 1 hour and the polymerization temperature 65° C. 2.13 kg of polypropylene were obtained. The activity of the metallocene was 69.0 kg of PP/g of metallocene×h.

VN=54.2 cm³/g, $M_w$=47,150, $M_w/M_n$=2.1, II=94.5%, SD=523 g/l.

EXAMPLE 4

The procedure of Example 1 was repeated, except that 39.3 mg (0.077 mmol) of rac-bisindenyl(phenylmethylsilyl) zirconium dichloride were used, the polymerization time was 1 hour, and the polymerization temperature 60° C. 1.50 kg of polypropylene were obtained. The activity of the metallocene was therefore 38.2 kg of PP/g of metallocene×h.

VN=60.8 cm³/g, $M_w$=56,100, $M_w/M_n$=2.2, II=95.4%, SD=487 g/l, no fines <50 µm.

EXAMPLE 5

The procedure of Example 1 was repeated, except that 28.3 mg (0.055 mmol) of rac-bisindenyl(phenylmethylsilyl) zirconium dichloride were used. The polymerization time was 3 hours and the polymerization temperature 60° C. 2.96 kg of polypropylene were obtained. The activity of the metallocene was therefore 34.9 kg of PP/g of metallocene ×h.

VN=59.5 cm³/g, $M_w$=54,100, $M_w/M_n$2.4, II=94.6%, SD=407 g/l, fines content of the powder <100 µm: 0.3%. The polymer product was obtained in the form of spherical particles having a narrow particle size distribution. Particle size distribution in the polymer:

| Sieve tray [µm] | Proportion [%] | Sum [%] |
|---|---|---|
| <100 | 0.3 | 0.3 |
| 100–200 | 22.4 | 22.7 |
| 200–300 | 71.9 | 94.6 |
| 300–400 | 2.6 | 97.2 |
| 400–500 | 0.3 | 97.5 |
| >500 | 2.5 | 100.0 |

$d_{50} = 250 \, \mu m, \, S = \ln \frac{d_{50}}{d_{15}} = 0.27.$

EXAMPLE 6 AND COMPARATIVE EXAMPLE B

In an experiment analogous to Example 4 and using rac-bisindenyl(dimethylsilyl)zirconium dichloride, a VN of 50.8 cm³/g, an $M_w$ of 44,900 and an $M_w/M_n$ of 2.2 were obtained. Repeating the same procedure with rac-ethylene-bisindenylzirconium dichloride only gave the following values:

VN=39.5 cm₃/g, $M_w$=27,600, $M_w/M_n$=2.2.

EXAMPLE 7

The procedure of Example 1 was repeated, except that 54.1 mg (0.106 mmol) of rac-bisindenyl(phenylmethylsilyl) zirconium dichloride were used. In addition, the polymerization was carried out at 50° C. for 1 hour and 20 minutes. 1.59 kg of polypropylene were obtained. The activity of the metallocene was therefore 22.0 kg of PP/g of metallocene× h.

VN=65.3 cm³/g, $M_w$=61,250, $M_w/M_n$=2.4.

EXAMPLE 8 AND COMPARATIVE EXAMPLE C

In an experiment analogous to Example 7 and using rac-bisindenyl(dimethylsilyl)zirconium dichloride, a polymer having a VN of 58.9 cm³/g, an $M_w$ of 54,450 and an $M_w/M_n$ of 2.6 was obtained. Repeating the same procedure with rac-ethylenebisindenylzirconium dichloride only gave the following values:

VN=43.2 cm³/g, $M_w$=36,100, $M_w/M_n$=2.4.

EXAMPLE 9

The procedure of Example 1 was repeated, except that 51.3 mg (0.10 mmol) of rac-bisindenyl(phenylmethylsilyl)zirconium dichloride were used. Polymerization was carried out at 30° C. for 3 hours. 690 g of polypropylene were obtained. The activity of the metallocene was therefore 4.5 kg of PP/g of metallocene×h.

VN=92.9 cm³/g, $M_w$=95,850, $M_w/M_n$=2.1.

EXAMPLE 10 AND COMPARATIVE EXAMPLE D

In an experiment analogous to Example 9 and using rac-bisindenyl(dimethylsilyl)zirconium dichloride, a polymer having a VN of 77.2 cm³/g, an $M_w$ of 76,500 and an $M_w/M_n$ of 2.5 was obtained. Repeating the same procedure with rac-ethylenebisindenylzirconium dichloride only gave the following values:

VN=54.7 cm₃/g, $M_w$=49,800, $M_w/M_n$ 2.3.

EXAMPLE 11

A dry 16 dm³ kettle was flushed with nitrogen and charged with 10 dm³ of liquid propylene. 50 cm³ of a methylaluminoxane solution in toluene (corresponding to 68 mmol of Al, average oligomerization degree n=23) were then added, and the batch was stirred at 30° C. for 15 minutes. At the same time, 47.9 mg (0.084 mmol) of rac-bisindenyl-(diphenylsilyl)zirconium dichloride were dissolved in 25 cm³ of a methylaluminoxane solution in toluene (34 mmol of Al) and preactivated by being left to stand for 15 minutes. The red solution was then added to the kettle. The polymerization system was brought to a temperature of 60° C. and maintained at this temperature for 1 hour. 2.56 kg of polypropylen were obtained. The activity of the metallocene was therefore 53.4 kg of PP/g of metallocene×h.

VN=57.4 cm³/g, $M_w$=45,500, $M_w/M_n$=2.1, II=97 % SD=330 g/l.

EXAMPLE 12

A dry 16 dm³ kettle was flushed with nitrogen and charged with 10 dm³ of liquid propylene. 29.4 cm³ of a methylaluminoxane solution in toluene (corresponding to 40 mmol of Al, average oligomerization degree n=23) were then added, and the batch was stirred at 30° C. for 15 minutes. At the same time, 13.8 mg (0.026 mmol) of rac-bisindenyl-(phenylvinylsilyl)zirconium dichloride were dissolved in 14.7 cm³ of a methylaluminoxane solution in toluene (20 mmol of Al) and preactivated by being left to stand for 15 minutes. The solution was then added to the kettle. The polymerization system was brought to a temperature of 70° C. and maintained at this temperature for 2 hours. 1.33 kg of polypropylene were obtained. The activity of the metallocene was therefore 48.2 kg of PP/g of metallocene×h.

VN=49.0 cm³/g, $M_w$=32,600, $M_w/M_n$=2.9, II=94%, SD=449 g/l.

EXAMPLE 13

The procedure of Example 12 was repeated, except that 56 mg (0.107 mmol) of rac-bisindenyl(phenylvinylsilyl)zirconium dichloride were used, the polymerization time was 105 minutes and the polymerization temperature 50° C. 1.39 kg of polypropylene were obtained. The activity of the metallocene was 14.2 kg of PP/g of metallocene×h.

VN=66 cm³/g, $M_w$=48,600, $M_w/M_n$=2.3.

EXAMPLE 14

The procedure of Example 12 was repeated, except that 10.3 mg (0.021 mmol) of rac-bisindenyl(dimethylgermyl)zirconium dichloride were used, the polymerization time was 1 hour, and the polymerization temperature 70° C. 2.83 kg of polypropylene were obtained. The activity of the metallocene was therefore 274.8 kg of PP/g of metallocene ×h.

VN=49 cm³/g, $M_w$=34,200, $M_w/M_n$=2.2, II=97.9%, SD=417 g/l.

EXAMPLE 15

The procedure of Example 14 was repeated, except that 15.7 mg (0.032 mmol) of the metallocene were used. The polymerization time was 2.5 hours and the polymerization temperature 60° C. 1.91 kg of polypropylene were obtained. The activity of the metallocene was therefore 48.7 kg of PP/g of metallocene×h.

VN=57.4 cm³/g, $M_w$=52,100, $M_w/M_n$=2.0, II=98%, SD=350 g/l.

We claim:

1. A compound comprising a metallocene of the formula (I)

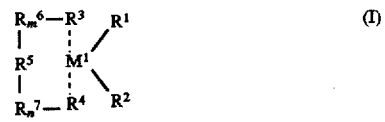

in which $M^1$ is titanium, zirconium, vanadium, niobium or tantalum, $R^1$ and $R^2$ are identical or different and denote a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_7$–$C_{40}$-alkylaryl group, or a $C_8$–$C_{40}$-arylalkenyl group, $R^3$ and $R^4$ are identical or different and denote a mononuclear or polynuclear hydrocarbon radical which can form a sandwich structure with the central atom, $R^5$ denotes

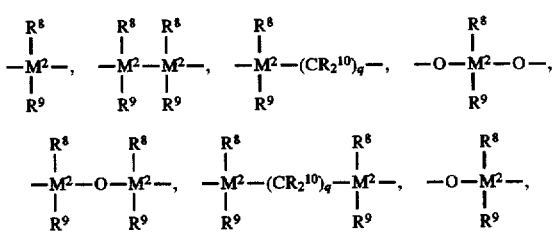

in which $R^8$ denotes a halogen atom, a $C_6$–$C_{10}$-aryl group, a $C_7$–$C_{40}$-arylalkyl group, a $C_8$–$C_{40}$-arylalkenyl group or a $C_7$–$C_{40}$-alkylaryl group, $R^9$ and $R^{10}$ are identical or different and denote a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$- arylalkyl group, a $C_8$–$C_{40}$-arylalkenyl group or a $C_7$–$C_{40}$-alkylaryl group or $R^8$ and $R^9$, or $R^8$ and $R^{10}$ each form a ring together with the atoms linking them, $M^2$ denotes silicon or germanium and q denotes 1, 2 or 3, or $R^5$ denotes

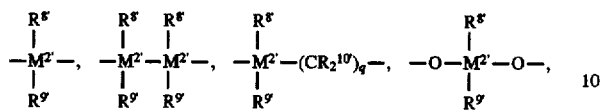

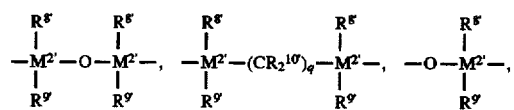

$=BR^8$, $=AlR^8$, —Sn—, —O—, $=SO_2$, $=NR^8$, $=PR^8$ or $=P(O)R^8$, in which $R^{8'}$, $R^{9'}$ and $R^{10'}$ are identical or different and denote a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{8'}$ and $R^{9'}$, or $R^{8'}$ and $R^{10'}$ each form a ring together with the atoms linking them, $M^{2'}$ denotes tin and q denotes 1, 2 or 3, $R^8$ denotes a halogen atom, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, $R^6$ and $R^7$ are identical or different and denote a $=CR^8R^9$ group, in which $R^8$ and $R^9$ have the abovementioned meaning, m and n are identical or different and denote zero, 1 or 2, where m+m is zero, 1 or 2.

2. The compound as claimed in claim 1, wherein $R^3$ and $R^4$ are identical.

3. The compound as claimed in claim 1, wherein $R^3$ and $R^4$ are identical or different and are indenyl, tetrahydroindenyl or cyclopentadienyl radicals.

4. The compound as claimed in claim 2, wherein $R^3$ and $R^4$ are indenyl radicals.

5. The compound as claimed in claim 1, wherein $R^3$ and $R^4$ are indenyl radicals.

6. The compound as claimed in claim 1, wherein $R^5$ is $=PR^8$.

7. The compound as claimed in claim 5, wherein $R^5$ is $=PR^8$.

* * * * *